(12) United States Patent
Tozzi et al.

(10) Patent No.: US 10,598,581 B2
(45) Date of Patent: *Mar. 24, 2020

(54) INLINE RHEOLOGY/VISCOSITY, DENSITY, AND FLOW RATE MEASUREMENT

(71) Applicant: ASPECT IMAGING LTD., Shoham (IL)

(72) Inventors: Emilio Javier Tozzi, Davis, CA (US); Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 148 days.

This patent is subject to a terminal disclaimer.

(21) Appl. No.: 15/292,247

(22) Filed: Oct. 13, 2016

(65) Prior Publication Data

US 2017/0097293 A1    Apr. 6, 2017

Related U.S. Application Data

(63) Continuation of application No. 14/073,142, filed on Nov. 6, 2013, now Pat. No. 9,494,503.

(51) Int. Cl.
*G01N 9/26* (2006.01)
*G01N 11/04* (2006.01)
(Continued)

(52) U.S. Cl.
CPC .............. *G01N 11/08* (2013.01); *G01N 9/26* (2013.01); *G01N 11/04* (2013.01); *G01N 24/08* (2013.01);
(Continued)

(58) Field of Classification Search
CPC .......... G01N 11/04; G01N 11/08; G01N 9/26; G01N 11/00; G01N 13/00;
(Continued)

(56) References Cited

U.S. PATENT DOCUMENTS 2,633,842 A    4/1953  Higgs
2,638,087 A    5/1953  Livsey
(Continued)

FOREIGN PATENT DOCUMENTS

CN    1236478    11/1999
CN    1291873    4/2001
(Continued)

OTHER PUBLICATIONS

ANSI/ISA SP76.00.2002 Miniature, Modular Mechanical Standard Specifications, 2002.
(Continued)

*Primary Examiner* — Randy W Gibson
*Assistant Examiner* — Gedeon M Kidanu
(74) *Attorney, Agent, or Firm* — Loeb & Loeb LLP (57) ABSTRACT

A system for performing inline measurements of flow rate, density, and rheology of a flowing fluid is disclosed, comprising: (a) a rheology measurement subsystem comprising: a horizontal tube of internal radius $r_H$; means for measuring a velocity profile of a test fluid flowing through said horizontal tube at a distance $x_0$ from its upstream end; and means for determining wall shear stress at a boundary between said flowing fluid and an inner surface of said horizontal tube; (b) a density measurement subsystem comprising: a vertical tube of internal radius $r_V$ in fluid connection with said horizontal tube; a pressure sensor for measuring the pressure of said test fluid within said vertical tube at a location $y_1$; and, (c) a pressure sensor for measuring the pressure of said test fluid within said vertical tube at a location $y_2$ downstream from $y_1$ and displaced vertically from $y_1$ by a distance $\Delta h$.

12 Claims, 2 Drawing Sheets

(51) Int. Cl.
*G01N 11/08* (2006.01)
*G01N 24/08* (2006.01)
*G01R 33/563* (2006.01)

(52) U.S. Cl.
CPC ...... *G01N 24/085* (2013.01); *G01R 33/56308* (2013.01)

(58) Field of Classification Search
CPC ......... G01N 2203/0623; G01N 24/085; G01N 24/08; G01N 2011/0026; C08K 5/20; C08L 57/08; C07C 2101/14; C07C 235/74; C07C 235/78; C07C 271/20; C07C 271/28; G06F 8/665; G11C 7/20; A61K 2039/53; A61K 2039/54; A61K 2039/552; A61K 2039/70; A61K 39/12; A61K 39/17; C07K 14/005; C12N 15/86; C12N 2710/16343; C12N 2720/10034; C12N 2760/18134; G01F 1/74; G01L 1/18; G01L 5/16; G01R 33/56308

See application file for complete search history.

(56) References Cited

U.S. PATENT DOCUMENTS

| | | | |
|---|---|---|---|
| 2,768,529 A | 10/1956 | Waterman et al. | |
| 3,175,403 A | 3/1965 | Nelson | |
| 3,989,630 A | 11/1976 | Walker | |
| 4,417,474 A * | 11/1983 | Elderton | G01N 9/26 73/438 |
| 4,468,622 A | 8/1984 | Frese et al. | |
| 4,697,594 A | 10/1987 | Mayo, Jr. | |
| 4,904,603 A | 2/1990 | Jones et al. | |
| 4,994,746 A | 2/1991 | Panosh | |
| 5,023,551 A | 6/1991 | Kleinberg et al. | |
| 5,145,189 A | 9/1992 | Pope | |
| 5,161,409 A | 11/1992 | Hughes et al. | |
| 5,168,226 A | 12/1992 | Hinks | |
| 5,208,534 A | 5/1993 | Okamoto et al. | |
| 5,280,243 A | 1/1994 | Miler | |
| 5,306,909 A | 4/1994 | Jones et al. | |
| 5,479,925 A | 1/1996 | Dumoulin et al. | |
| 5,532,593 A * | 7/1996 | Maneval | G01N 11/08 324/300 |
| 5,557,103 A | 9/1996 | Hughes et al. | |
| 5,557,201 A | 9/1996 | Kleinberg et al. | |
| 5,696,448 A | 12/1997 | Coates et al. | |
| 5,705,927 A | 1/1998 | Sezginer et al. | |
| 5,757,187 A | 5/1998 | Wollin | |
| 5,784,333 A | 7/1998 | Tang et al. | |
| 5,800,335 A | 9/1998 | Koch et al. | |
| 5,827,952 A | 10/1998 | Mansure et al. | |
| 5,986,454 A | 11/1999 | Leifer | |
| 6,069,106 A | 5/2000 | Hettinger, Jr. | |
| 6,090,728 A | 7/2000 | Yenni, Jr. et al. | |
| 6,107,796 A | 8/2000 | Prammer | |
| 6,178,807 B1 | 1/2001 | Baldwin et al. | |
| 6,215,304 B1 | 4/2001 | Slade | |
| 6,268,726 B1 | 7/2001 | Prammer et al. | |
| 6,362,619 B2 | 3/2002 | Prammer et al. | |
| 6,412,337 B1 * | 7/2002 | Arzate | G01N 11/08 73/54.02 |
| 6,421,337 B1 | 7/2002 | Rao et al. | |
| 6,452,390 B1 | 9/2002 | Wollin | |
| 6,507,191 B1 | 1/2003 | Eguchi et al. | |
| 6,518,758 B1 | 2/2003 | Speier et al. | |
| 6,549,007 B1 | 4/2003 | Hills et al. | |
| 6,550,327 B1 * | 4/2003 | Van Berk | G01N 9/26 73/152.18 |
| 6,646,437 B1 | 11/2003 | Chitale et al. | |
| 6,807,857 B2 * | 10/2004 | Storm, Jr. | G01N 9/26 73/438 |
| 6,856,132 B2 | 2/2005 | Appel et al. | |
| 6,907,375 B2 | 6/2005 | Guggari et al. | |
| 6,913,827 B2 | 7/2005 | George et al. | |
| 6,952,096 B2 | 10/2005 | Freedman | |
| 7,075,366 B2 | 7/2006 | Deem et al. | |
| 7,295,933 B2 | 11/2007 | Gysling et al. | |
| 7,352,179 B2 | 4/2008 | Chen et al. | |
| 7,486,071 B2 | 2/2009 | Care et al. | |
| 7,489,132 B2 | 2/2009 | Arik et al. | |
| 7,570,058 B1 | 8/2009 | Wong et al. | |
| 7,823,656 B1 | 11/2010 | Williams | |
| 7,908,034 B2 | 3/2011 | Gray | |
| 7,921,731 B2 * | 4/2011 | Bajikar | G01L 1/18 73/760 |
| 8,024,962 B2 * | 9/2011 | Tonmukayakul | G01N 33/241 73/54.28 |
| 8,143,887 B2 | 3/2012 | Pusiol | |
| 8,256,532 B2 | 9/2012 | Gray | |
| 8,373,412 B2 | 2/2013 | Kruspe et al. | |
| 8,461,842 B2 | 6/2013 | Thuringer et al. | |
| 8,469,118 B2 | 6/2013 | Passade-Boupat et al. | |
| 8,736,263 B2 | 5/2014 | Minh | |
| 8,763,170 B1 | 7/2014 | Ungarsohn | |
| 8,763,710 B2 | 7/2014 | Graue | |
| 8,791,695 B2 | 7/2014 | Balcom et al. | |
| 8,807,084 B2 | 8/2014 | Rapoport et al. | |
| 8,812,236 B1 | 8/2014 | Freeman et al. | |
| 8,851,018 B2 | 10/2014 | Rapoport et al. | |
| 8,896,310 B2 | 11/2014 | Rapoport | |
| 9,194,972 B2 | 11/2015 | Van Der Zwaag et al. | |
| 9,448,093 B2 | 9/2016 | Rapoport | |
| 9,476,847 B2 | 10/2016 | Trygstad et al. | |
| 2002/0173717 A1 | 11/2002 | Rohling et al. | |
| 2003/0006768 A1 | 1/2003 | Kleinberg et al. | |
| 2004/0017193 A1 | 1/2004 | Speier | |
| 2004/0090230 A1 | 5/2004 | Appel et al. | |
| 2004/0108852 A1 | 6/2004 | de Swiet | |
| 2004/0116799 A1 | 6/2004 | Srinivasan | |
| 2004/0127786 A1 | 7/2004 | Schmit et al. | |
| 2004/0140800 A1 | 7/2004 | Madio et al. | |
| 2004/0169512 A1 | 9/2004 | Jara | |
| 2005/0011283 A1 | 1/2005 | Gysling et al. | |
| 2005/0024053 A1 | 2/2005 | Care et al. | |
| 2005/0030020 A1 | 2/2005 | Siess et al. | |
| 2005/0044957 A1 | 3/2005 | Muldowney | |
| 2005/0113668 A1 | 5/2005 | Srinivasan | |
| 2005/0203420 A1 | 9/2005 | Kleen et al. | |
| 2006/0011547 A1 | 1/2006 | Bell | |
| 2006/0279283 A1 | 12/2006 | Nistler et al. | |
| 2007/0061081 A1 | 3/2007 | Moran | |
| 2007/0164737 A1 | 7/2007 | Pusiol | |
| 2007/0188172 A1 | 8/2007 | Garwood et al. | |
| 2007/0232894 A1 | 10/2007 | Feenan | |
| 2008/0136049 A1 | 6/2008 | Sen et al. | |
| 2008/0136409 A1 | 6/2008 | Sen et al. | |
| 2008/0174309 A1 | 7/2008 | Pusiol et al. | |
| 2008/0180226 A1 | 7/2008 | Schmidt | |
| 2008/0189456 A1 | 8/2008 | Schmidt et al. | |
| 2008/0257413 A1 * | 10/2008 | Noureldin | F01K 13/02 137/10 |
| 2009/0004748 A1 | 1/2009 | Ganesan | |
| 2009/0044638 A1 * | 2/2009 | Gysling | G01F 1/34 73/861.42 |
| 2009/0050318 A1 | 2/2009 | Kasevich | |
| 2009/0050369 A1 | 2/2009 | Pop et al. | |
| 2009/0072824 A1 | 3/2009 | Romero | |
| 2009/0090504 A1 * | 4/2009 | Weightman | E21B 43/26 166/250.01 |
| 2009/0194330 A1 | 8/2009 | Gray | |
| 2009/0312963 A1 * | 12/2009 | Najim Al-Khamis | G01N 9/26 702/47 |
| 2009/0312964 A1 * | 12/2009 | Najim Al-Khamis | E21B 43/34 702/50 |
| 2010/0133488 A1 | 6/2010 | Giakos | |
| 2010/0154325 A1 | 6/2010 | Boesel et al. | |
| 2010/0264914 A1 | 10/2010 | Minh | |
| 2010/0271019 A1 | 10/2010 | Anand et al. | |
| 2011/0036584 A1 * | 2/2011 | Weightman | E21B 43/26 166/308.1 |

(56) References Cited

U.S. PATENT DOCUMENTS

| | | |
|---|---|---|
| 2011/0125333 A1 | 5/2011 | Gray |
| 2011/0162652 A1 | 7/2011 | Rapoport |
| 2011/0185795 A1* | 8/2011 | Colquhoun ............ G01N 11/04 73/54.02 |
| 2011/0186049 A1 | 8/2011 | Rapoport |
| 2011/0234347 A1 | 9/2011 | Rapoport |
| 2011/0270525 A1 | 11/2011 | Hunter |
| 2011/0296911 A1* | 12/2011 | Moore .................... G01N 9/26 73/32 R |
| 2011/0304333 A1 | 12/2011 | Rapoport |
| 2012/0013335 A1* | 1/2012 | Saasen ................. G01N 24/08 324/303 |
| 2012/0024602 A1 | 2/2012 | Larson |
| 2012/0065491 A1 | 3/2012 | Borgert et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0092007 A1 | 4/2012 | Li et al. |
| 2012/0119742 A1 | 5/2012 | Rapoport |
| 2012/0205288 A1 | 8/2012 | Jia et al. |
| 2012/0212224 A1 | 8/2012 | Burns |
| 2012/0265050 A1 | 10/2012 | Wang |
| 2013/0009959 A1 | 1/2013 | Calamante et al. |
| 2013/0025062 A1 | 1/2013 | Esch |
| 2013/0060474 A1 | 3/2013 | Venkataramanan et al. |
| 2013/0079624 A1 | 3/2013 | Rapoport |
| 2013/0090855 A1 | 4/2013 | Rasmus et al. |
| 2013/0091941 A1 | 4/2013 | Huh et al. |
| 2013/0109956 A1 | 5/2013 | Rapoport |
| 2013/0123639 A1 | 5/2013 | Ando |
| 2013/0124106 A1 | 5/2013 | Rogel et al. |
| 2013/0154644 A1 | 6/2013 | Virtanen et al. |
| 2013/0179092 A1 | 7/2013 | Martin et al. |
| 2013/0237803 A1 | 9/2013 | Rapoport |
| 2013/0271135 A1 | 10/2013 | Ozen et al. |
| 2013/0328559 A1 | 12/2013 | Rapoport |
| 2013/0328560 A1 | 12/2013 | Rapoport |
| 2013/0328563 A1 | 12/2013 | Rapoport |
| 2013/0345994 A1* | 12/2013 | Wiklund .................. G01F 1/34 702/46 |
| 2014/0049257 A1 | 2/2014 | Rapoport |
| 2014/0050824 A1 | 2/2014 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0253116 A1 | 9/2014 | Freedman et al. |
| 2014/0257081 A1 | 9/2014 | Rapoport |
| 2014/0262957 A1 | 9/2014 | Gong et al. |
| 2014/0266203 A1 | 9/2014 | Rapoport |
| 2014/0300358 A1 | 10/2014 | Rapoport |
| 2014/0309951 A1* | 10/2014 | Alvarez Vallejos ... G01N 11/08 702/47 |
| 2014/0333304 A1 | 11/2014 | Jensen |
| 2014/0354299 A1 | 12/2014 | Rapoport |
| 2014/0378821 A1 | 12/2014 | Rapoport et al. |
| 2014/0378825 A1 | 12/2014 | Rapoport et al. |
| 2015/0059157 A1 | 3/2015 | Rapoport |
| 2015/0059655 A1 | 3/2015 | Rapoport |
| 2015/0065788 A1 | 3/2015 | Rapoport |
| 2015/0084630 A1 | 3/2015 | Rapoport |
| 2015/0087051 A1 | 3/2015 | Rapoport |
| 2015/0112186 A1 | 4/2015 | Rapoport et al. |
| 2015/0130460 A1 | 5/2015 | Valori et al. |
| 2015/0137812 A1 | 5/2015 | Rapoport |
| 2015/0141799 A1 | 5/2015 | Rapoport et al. |
| 2015/0168519 A1 | 6/2015 | Rapoport |
| 2015/0268374 A1 | 9/2015 | Rapoport |
| 2015/0320888 A1 | 11/2015 | Yoneda et al. |
| 2015/0357694 A1 | 12/2015 | Denis et al. |
| 2015/0377998 A1 | 12/2015 | Bendel |
| 2016/0053187 A1 | 2/2016 | Hayasaka et al. |
| 2016/0108687 A1 | 4/2016 | Rapoport |
| 2016/0109539 A1 | 4/2016 | Mardor et al. |
| 2017/0243681 A1 | 8/2017 | Somerkoski et al. |

FOREIGN PATENT DOCUMENTS

| | | |
|---|---|---|
| CN | 1422324 | 6/2003 |
| CN | 1427877 | 7/2003 |
| CN | 1590994 | 3/2005 |
| CN | 101421636 | 4/2009 |
| CN | 101556234 | 10/2009 |
| CN | 101581717 | 11/2009 |
| CN | 101632584 | 1/2010 |
| CN | 101793147 | 8/2010 |
| CN | 101907586 | 12/2010 |
| CN | 103217362 | 7/2013 |
| CN | 103542899 | 1/2014 |
| CN | 103712071 | 4/2014 |
| CN | 103954639 | 7/2014 |
| DE | 202014105273 | 12/2014 |
| EP | 0 210 289 | 2/1987 |
| EP | 0770660 | 5/1997 |
| EP | 0835463 | 8/2003 |
| EP | 1532460 | 6/2004 |
| EP | 2604996 | 6/2013 |
| EP | 2927420 A2 | 10/2015 |
| EP | 2927420 A3 | 2/2016 |
| GB | 2341685 A | 7/1999 |
| RU | 2229023 | 5/2004 |
| RU | 2285119 | 10/2006 |
| RU | 2367982 | 9/2009 |
| SU | 876954 | 10/1981 |
| SU | 1041677 | 9/1983 |
| WO | WO1995018387 | 7/1995 |
| WO | WO2001002832 | 1/2001 |
| WO | WO0151588 | 7/2001 |
| WO | WO2001051588 | 7/2001 |
| WO | WO2001051589 | 7/2001 |
| WO | WO2004053513 | 6/2004 |
| WO | WO2008008447 | 1/2008 |
| WO | WO2008043373 | 4/2008 |
| WO | WO2010000055 | 1/2010 |
| WO | WO2011095600 | 8/2011 |
| WO | WO2012004797 | 1/2012 |
| WO | WO2013009299 | 1/2013 |
| WO | WO2013162400 | 10/2013 |
| WO | WO2013179092 | 12/2013 |
| WO | WO2014004573 | 1/2014 |
| WO | WO2014027350 | 2/2014 |
| WO | WO2014203245 | 12/2014 |
| WO | WO2015070872 | 5/2015 |

OTHER PUBLICATIONS

Bennett, et al. A nondestructive technique for determining thermal properties of thermal barrier coatings, Journal of Applied Physics, 2005, 97, 013520,1-12.

Caprihan, et al. Flow measurements by NMR, Physics Reports, (Review Section of Physics Letters)1990, 198, No. 4, 195-235.

Coussot et al., Rheological behavior of drilling muds, characterization using MRI visualization, Oil & Gas Science and Technology, Rev. IFP, 2004, vol. 59, No. 1, 23-29.

Doble et al., Optimization of the relaxivity of MRI contrast agents: effects of poly(ethylene glycol) chains on the water-exchange rates of Gd complexes, J. Am. Chem. Soc. 2001, 123, 10758-10759.

Dyverfeldt et al., Quantification of intravoxel velocity standard deviation and turbulence intensity by generalizing phase-contrast MRI, Magnetic Resonance in Medicine, 2006, 56:850-858.

Felemban, et al. RFID for Oil and Gas Industry: Applications and (56) References Cited

OTHER PUBLICATIONS

Challenges, International Journal of Engineering and Innovative Technology (IJEIT) vol. 3, Issue 5, Nov. 2013, 20-85.

Goloshevsky et al., Nuclear magnetic resonance imaging for viscosity measurements of non-Newtonian fluids using a miniaturized RF coil, Meas. Sci. Technol., 2005, 16:513-518.

Gunnerod et al., Highly automated drilling fluids system improves HSE and efficiency, reduced personnel needs, Drilling Contractor, Heath, Safety & Environment, Jan./Feb. 2009, 73-77.

Hou et al., Review Article, Instrument techniques for rheometry, Review of Scientific Instruments, 2005, 76, 101101, 1-19.

Hsu et al., Encoding to the longitudinal magnetization for MR imaging and flow velocity mapping, Journal of Magnetic Resonance, 2006, 183, 41-49.

International Electromechanical Commission in publication, IEC 62339-1:2006, 2006.

Kose, Katsumi, Visualization of local shearing motion in turbulent fluids using echo-planar imaging, Journal of Magnetic Resonance, 1992, 96, 596-603.

Lucas et al., An Iterative Image Registration Technique with an Application to Stereo Vision, Proceedings of Imaging Understanding Workshop, pp. 121-130 (1981).

MacGowan et al., Fast measurements of the motion and velocity spectrum of blood using MR tagging, Magnetic Resonance in Medicine, 2001, 45:461-469.

Ocali et al., Ultimate intrinsic signal-to-noise ratio in MRI, MRM, 1998, 39:462-473.

Pohost et al., Nuclear magnetic resonance imaging: With or without nuclear?, JACC Mar. 1986, vol. 7, No. 3, 709-710.

Poulichet et al., Optimisation and realisation of a portable NMR apparatus and Micro Antenna for NMR, DTIP, May 2011, 11-13, Aix-en-Provence, France.

Prammer et al., The magnetic resonance while-drilling tool: theory and operation, Society of Engineers, 2000, SPE62981, 1-8.

Rabideau et al., The extrusion of a model yield stress fluid imaged by MRI velocimetry, J. Non-Newtonian Fluid Mech, 2010, 165, 394-408.

Shadday Jr., M.A., Recommendations for rheological testing and modelling of DWPF meter feed slurries (U), Engineering & Materials Technology Dept., WSRC-TR-94-0357, 1994 pp. 1-45.

Arola, Darren F., et al. "Use of nuclear magnetic resonance imaging as a viscometer for process monitoring." Chemical engineering science 52.13 (1997): pp. 2049-2057.

Güzel, B., I. Frigaard, and D. M. Martinez. "Predicting laminar—turbulent transition in Poiseuille pipe flow for non-Newtonian fluids." Chemical Engineering Science 64.2 (2009):pp. 254-264.

Poole, R. J., and B. S. Ridley. "Development-length requirements for fully developed laminar pipe flow of inelastic non-Newtonian liquids." *Journal of Fluids Engineering* 129.10 (2007): 1281-1287.

Degré, Guillaume, et al. "Rheology of complex fluids by particle image velocimetry in microchannels." Applied Physics Letters 89.2 (2006): 024104.

International Search Report for PCT Application No. PCT/IL2014/050947 dated Apr. 15, 2015.

Dogan, Nihan, Michael J. McCarthy, and Robert L. Powell, "Measurement of polymer melt rheology using ultrasonics-based in-line rheometry." *Measurement Science and Technology* 16.8 (2005): p. 1684.

Notice of Allowance for U.S. Appl. No. 14/073,142 dated Jul. 15, 2016.

Bird et al., "Transport Phenomena", Chapter 2, Shell Momentum Balances and Velocity Distributions in Laminar Flow, Dec. 31, 2002, XP-002768172, Wiley, p. 54.

Bradley Jr. et al., The appearance of rapidly flowing blood on magnetic resonance images, AJR, Dec. 1984, 143:1167-1174.

Yan, Jienian, Drilling Fluids Technology, May 31, 2001, China University of Petroleum Press, pp. 61-66.

Li et al., Pipe flow of aqueous polyacrylamide solutions studies by means of nuclear magnetic resonance imaging, J. Non-Newtonian Fluid Mech., 57 (1995) 155-175.

Fumoto et al., Catalytic cracking of heavy oil over a complex metal oxide catalyst in a steam atmosphere, American chemical Society, 2012, Chapter 6, ACS Symposium Series, pp. 75-85.

Koen Roelstraete: "Nuclear Magnetic 1-3 Resonance Analysis On-line; Overview of the technology. benefits. solutions and applications to the Refinery". Prove Interlaboratorio Prodotti Petroliferi Milano. Nov. 9, 2011. Jan. 29, 2011 pp. 1-52.

Macosko, C. W., Rheology Principles, Measurements and Applications, VCH: New York, 1993, pp. 1-9.

\* cited by examiner

INLINE RHEOLOGY/VISCOSITY, DENSITY, AND FLOW RATE MEASUREMENT

CROSS REFERENCE TO RELATED APPLICATIONS

This patent application is a continuation of, claims the benefit of and priority to co-pending U.S. patent application Ser. No. 14/073,142, filed on Nov. 6, 2013, the entire contents of which is incorporated herein by reference in their entirety.

FIELD OF THE INVENTION

The invention disclosed herein is related in general to means and methods for measuring physical properties of flowing fluids. Specifically, it is related to means and methods for performing inline multiple-parameter measurements.

BACKGROUND OF THE INVENTION

Control and monitoring of processes involving the flow through tubes of fluids that may be of complex rheology is an important problem in such diverse industrial settings as preparation and processing of food, manufacture of personal care products, oil exploration, extraction, and production, production of coatings, and biotechnology. Ideally, measurements should be made non-invasively and in real time so that defects or variations in quality can quickly be identified and corrected, and all of the parameters of interest would be obtained by a single measurement device. Among the fluid parameters of interest are the flow rate, density, and viscosity. Viscosity in particular is difficult to measure on-line, as particulate matter in the fluid tends to interfere with the operation of most conventional viscometers, and many fluids of interest have viscosities that depend on the shear rate or shear rate history and hence cannot be described by a single-valued viscosity. Construction of rheograms (flow curves) for such fluids requires more sophisticated instrumentation than a simple viscometer, but the instruments generally used for making the measurements needed to construct rheograms, which generally contain narrow gaps or vibrating elements, are unsuitable for fluids that may contain particles or sticky deposits.

A number of systems for measuring fluid density are known that are based on measurement of hydrostatic pressure and means to take into account frictional losses in the pipe. For example, U.S. Pat. No. 2,768,529 discloses a continuous density measurement system based on measuring pressure differences in vertical tubes in series. The differential measurements are arranged such that subtraction of pressure loss due to friction is possible. U.S. Pat. Nos. 3,175,403 and 4,417,474 disclose continuous density measurement systems based on measurement of pressure differences in a vertical tube and a horizontal tube. The horizontal tube permits subtraction of frictional pressure losses in the vertical tube. These instruments only measure density, however, and do not provide information about rheology or flow rate. Furthermore, the methods disclosed in these patents require that all of the tubes be of the same diameter, since the rheology of the fluids is unknown.

Coriolis-type flow meters an example of a type of instrument well-known in the art for the measurement of both flow rates and density. These instruments, while multi-parametric, do not measure rheology, and are susceptible to errors if the mass of the vibrating element changes due to solid deposits. In addition, at very low flow rates, these instruments have large errors, reducing the range of flow rates that can be measured by a single instrument; the instrument must be selected to match the process conditions and a larger or smaller instrument may be needed if the conditions change.

A number of rheometers have been described that are based on non-invasive velocimetry methods. For example, U.S. Pat. No. 5,532,593 discloses a rheometer based on nuclear magnetic resonance A system based on ultrasound is described in Dogan et al., "Measurement of Polymer Melt Rheology Using Ultrasonics-Based In-line Rheometry," Meas. Sci. Technol. 16 (2005) 1684-1690. An optically based method is described in Degre et al., "Rheology of Complex Fluids by Particle Image Velocimetry in Microchannels," Appl. Phys. Lett. 89 (2006) 024104. These systems can measure rheology and flow rate even for difficult systems containing large particles, and a single instrument can be calibrated electronically to cover a wide range of flow rates, but they cannot measure fluid density.

A single integrated system that can perform simultaneous accurate non-invasive in-line, real-time measurements of flow rate, density, and rheology even for fluids of complex rheology or fluids that may contain particulate matter, that does not require that all of the tubes or pipes through which the liquid flows be of the same diameter, and that can perform accurate measurements over wide ranges of flow rates, remains a long-felt, but as yet unmet, need.

SUMMARY OF THE INVENTION

The system herein disclosed is designed to meet this long-felt need. The system comprises a horizontal tube for measurement of rheology and at least one vertical tube for measurement of density. Due to the rheology already having been measured in the horizontal tube, the tube or tubes that make up the vertical density measurement section may be of larger diameter that the horizontal tubes. Advantages of having larger diameter tubes in the vertical section include reduced pumping energy due to smaller frictional losses and lower sensitivity to flow-related frictional effects in the vertical tube, making the density measurements more precise and less susceptible to errors due to flow fluctuations. Having a horizontal tube (i.e. in the section of the system that measures rheology) of smaller diameter has the advantage that it provides a strong (and hence easily detectable) signal for measurement of pressure drop even over a short distance, and that it requires smaller, less costly imaging equipment; for example, the costs of MRI magnets increase nonlinearly with bore size.

It is thus an object of the present invention to disclose a system for performing inline measurements of flow rate, density, and rheology of a flowing fluid, wherein said system comprises: (a) a rheology measurement subsystem (100), said rheology measurement subsystem comprising: a horizontal tube (110) of internal radius $r_H$ having an upstream end and a downstream end; a velocity profile measurement device (130) configured to measure a velocity profile of a test fluid flowing through said horizontal tube at a distance $x_0$ from said upstream end; and, wall shear stress determining means for determining wall shear stress at a boundary between said flowing fluid and an inner surface of said horizontal tube (110); (b) a density measurement subsystem (200), said density measurement subsystem comprising: a vertical tube (210) of internal radius $r_V$ in fluid connection with said horizontal tube; a first pressure sensor (220) configured to measure pressure of said test fluid within said vertical tube at a location $y_1$; and, (c) a second pressure sensor (230) configured to measure pressure of said test fluid within said vertical tube at a location $y_2$ downstream from $y_1$ and displaced vertically from $y_1$ by a distance $\Delta h$.

In some preferred embodiments of the invention, said wall shear stress determining means comprise: (a) a third pressure sensor (120), said third pressure sensor configured to measure pressure of said test fluid within said horizontal tube at a horizontal distance $x_1 < x_0$ from said upstream end; and, (b) a fourth pressure sensor (140) located downstream of said velocity profile measurement device, said fourth pressure sensor configured to measure pressure of said test fluid within said horizontal tube at a horizontal distance $x_2 > x_0$ from said upstream end. In some especially preferred embodiments of the invention, said wall shear stress determining means comprise a direct wall stress sensor.

In preferred embodiments of the system, $r_V > r_H$. In some preferred embodiments of the system, said system comprises a differential pressure sensor that comprises said first pressure sensor and said second pressure sensor. In some preferred embodiments of the system, said system comprises a differential pressure sensor that comprises said third pressure sensor and said fourth pressure sensor. In some embodiments of the system, said density measurement subsystem is downstream of said rheology measurement subsystem. In other embodiments of the system, said measurement subsystem is upstream of said rheology measurement subsystem.

It is a further object of the present invention to disclose the system as defined in any of the above, further comprising a control subsystem (400), said control subsystem comprising pressure sensor reading means in independent electronic connection with each of said pressure sensors; and velocity profile measurement device control means electronically connected to said velocity profile measurement device. In some preferred embodiments of the system, said control subsystem additionally comprises at least one of (a) memory means for storing readings obtained by said pressure sensors; (b) memory means for storing readings obtained by said velocity profile measurement device; and (c) numerical calculation means programmed to perform at least one operation selected from the group consisting of integration, differentiation, unit conversions, computing fluid density according to a preprogrammed algorithm; and, computing fluid rheological properties according to a preprogrammed algorithm.

It is a further object of the present invention to disclose the system as defined in any of the above, wherein said velocity profile measurement device is selected from the group consisting of an imaging NMR spectrometer; an ultrasound velocimetry system; an optical velocimetry system; a pitot tube array; and an array of thermal flow sensors. In some preferred embodiments of the invention, said velocity profile measurement device is an NMR spectrometer. In some preferred embodiments of the invention, said velocity profile measurement device is an imaging NMR spectrometer that comprises a permanent magnet. In some preferred embodiments of the invention in which said velocity profile measurement device is an imaging NMR spectrometer, said imaging NMR spectrometer is configured to perform imaging of a flow of said test fluid by using a pulsed gradient spin echo sequence.

It is a further object of the present invention to disclose the system as defined in any of the above, further comprising a pump (610) configured to pump fluid through both said horizontal tube and said vertical tube. In some embodiments of the invention, the pump is located between said density measurement system and said rheology measurement subsystem. In some embodiments of the invention, the pump is located downstream of both said horizontal tube and said vertical tube. In some embodiments of the invention, the pump is located upstream of both said horizontal tube and said vertical tube.

It is a further object of the present invention to disclose the system as defined in any of the above, additionally comprising a flow measurement subsystem, said flow measurement subsystem comprising: a horizontal flow measurement tube (510) of internal radius $r_F$; a fifth pressure sensor (520) configured to measure pressure of said test fluid within said horizontal flow measurement tube at a location $x_3$; a sixth pressure sensor (530) configured to measure pressure of said test fluid within said horizontal flow measurement tube at a location $x_4$ downstream of said location $x_3$; an upstream branch point in said horizontal flow measurement tube, located upstream of said fifth pressure sensor, said upstream branch point in fluid connection with the furthest upstream point of said rheology measurement subsystem and said density measurement subsystem; and, a downstream branch point in said horizontal flow measurement tube, located downstream of said upstream branch point, said downstream branch point in fluid connection with the furthest downstream point of said rheology measurement subsystem and said density measurement subsystem. In some embodiments of the system, said downstream branch point is located downstream of said sixth pressure sensor. In some embodiments of the system, said downstream branch point is located upstream of said fifth pressure sensor. In some embodiments of the system, said system comprises a differential pressure sensor comprising said fifth pressure sensor and said sixth pressure sensor.

It is a further object of the present invention to disclose the system as defined in any of the above, wherein $r_F > r_H$.

It is a further object of the invention to disclose a method for performing inline rheology and density measurements on a test fluid having a density $\rho$, comprising: flowing said test fluid through a horizontal tube of internal radius $r_H$ having an upstream end and a downstream end; measuring a velocity profile $v(r)$ at a distance $x_0$ from said upstream end for at least one value of $r$, $0 \leq r \leq r_H$; determining a shear rate $\dot{\gamma}(r)$; calculating shear stress as a function of shear rate (rheogram) $\tau(\dot{\gamma})$ for at least one value of $r$, $0 \leq r \leq r_H$; calculating at least one rheology parameter of said test fluid $$\eta(\dot{\gamma}) = \frac{\tau(\dot{\gamma})}{\dot{\gamma}};$$

flowing said test fluid into a vertical tube of internal radius $r_V$; and determining said density $\rho$ of said test fluid in said vertical tube.

It is a further object of the invention to disclose such a method, wherein said step of determining a shear rate comprises differentiating said velocity profile with respect to radius, $$\dot{\gamma}(r) = \left| \frac{dv}{dr} \right|.$$

It is a further object of the invention to disclose such a method as defined in any of the above, wherein said step of calculating a radius-dependent shear stress comprises: measuring a pressure difference $\Delta P_H$ between pressures of said test fluid measured at two locations $x_1$ and $x_2$, $x_1$ upstream of $x_0$, $x_2$ downstream of $x_0$; calculating shear stress as a function of radius $$\tau(r) = \frac{\Delta P_H}{2L} r,$$

where $L=x_2-x_1$; and combining said shear stress as a function of radius with said shear rate as a function of radius to produce a rheogram (curve of shear stress as a function of shear rate).

In some preferred embodiments of the method, said step of flowing said test fluid through a horizontal tube comprises flowing said test fluid through a horizontal tube under conditions of laminar flow. In some embodiments of the method, said step of flowing said test fluid through a horizontal tube precedes said step of flowing said test fluid through a vertical tube. In some embodiments of the method, said step of flowing said test fluid through a vertical tube precedes said step of flowing said test fluid through a horizontal tube.

It is a further object of the invention to disclose the method as defined in any of the above, wherein said step of passing said test fluid into a vertical tube comprises passing said test fluid into a vertical tube of internal radius $r_V > r_H$.

It is a further object of the invention to disclose the method as defined in any of the above, wherein said step of determining said density comprises (a) measuring a pressure difference $\Delta P_V = P_1 - P_2$, where $P_1$ is the pressure of said test fluid at a first location $y_1$ and $P_2$ is the pressure of said test fluid at a second location $y_2$ downstream of $y_1$ and separated from $y_1$ by a vertical distance $\Delta h = h_1 - h_2$ where $h_1$ is the height of location $y_1$ and $h_2$ the height of location $y_2$; and (b) calculating said density $\rho$ from the relation $$\rho = \frac{1}{g\Delta h}\left(\frac{2\tau_w}{r_v}|\Delta h| - \Delta P_v\right)$$

where $\tau_w$ represents wall stress within said vertical tube and g represents acceleration due to gravity. In some preferred embodiments of the invention, said step of calculating said density comprises calculating said wall stress within said vertical tube $\tau_W$ according to the relation $$Q = \frac{\pi r_V^3}{\tau_W^3}\int_0^{\tau_W}|\dot{\gamma}|\tau^2 d\tau.$$

It is a further object of this invention to disclose a method as defined in any of the above, further comprising: passing said test fluid through a horizontal flow measurement tube; and, calculating a flow rate of said test fluid through said horizontal flow measurement tube. It is a further object of the invention to disclose the method as defined in any of the above, wherein said step of measuring a velocity profile comprises using a velocity profile measurement device selected from the group consisting of an NMR spectrometer; an ultrasound velocimetry system; an optical velocimetry system; a pitot tube array; and an array of thermal flow sensors to measure said velocity profile.

It is a further object of the invention to disclose the method as defined in any of the above, wherein said step of measuring a velocity profile comprises using a velocity profile measurement device selected from the group consisting of an NMR spectrometer; an ultrasound velocimetry system; an optical velocimetry system; a pitot tube array; and an array of thermal flow sensors to measure said velocity profile. In some preferred embodiments of the invention, said step of measuring a velocity profile comprises (a) passing said test fluid through of an NMR spectrometer; and (b) imaging said test fluid as it passes through said NMR spectrometer via an NMR imaging technique. In some preferred embodiments of the invention, said step of passing said test fluid through an NMR spectrometer comprising a permanent magnet. In some preferred embodiments of the invention, said NMR imaging technique comprises a pulsed gradient spin echo sequence.

It is a further object of the invention to disclose the method as defined in any of the above, wherein said test fluid is selected from the group consisting of single-component liquids, mixtures of liquids, solutions, suspensions, emulsions, colloids, slurries, pastes, creams, foams, media containing one or more liquids mixed with gas bubbles, media containing one or more liquids mixed with solid matter, and media containing one or more liquids mixed with gas and solid matter.

It is a further object of the invention to disclose the method as defined in any of the above, wherein said test fluid is non-Newtonian.

It is a further object of the invention to disclose the method as defined in any of the above, wherein said test fluid is a yield-stress material.

It is a further object of the invention to disclose the method as defined in any of the above, wherein said test fluid comprises a fluid selected from the group consisting of oil-based drilling fluid, water-based drilling fluid, synthetic drilling fluid, fracturing fluid, crude oil, refined oil, an oil/water mixture, any of the above containing particulate matter, and any of the above to which a viscosifier has been added.

It is a further object of the invention to disclose the method as defined in any of the above, wherein said test fluid is a potable liquid.

It is a further object of the invention to disclose the method as defined in any of the above, wherein said test fluid is an edible material that can be pumped through a tube. In some preferred embodiments of the invention, said edible material is selected from the group consisting of ice cream, cookie dough, and pie filling.

It is a further object of the invention to disclose the method as defined in any of the above, wherein said test fluid is selected from the group consisting of personal care products and fluid ingredients of personal care products. In some preferred embodiments of the invention, said test fluid is selected from the group consisting of pharmaceutical creams, ointments, and semi-liquid products.

It is a further object of the invention to disclose the method as defined in any of the above, wherein said test fluid is a material from a biotechnological process. In some preferred embodiments of the invention, said material is selected from the group consisting of a medium undergoing fermentation, a medium undergoing a biotransformation, material undergoing an enzymatic reaction, and biological material undergoing a non-enzymatic chemical reaction.

It is a further object of the invention to disclose the method as defined in any of the above, wherein said test fluid is a coating.

It is a further object of the invention to disclose the method as defined in any of the above, wherein said test fluid comprises a material undergoing polymerization or depolymerization that causes rheological changes.

It is a further object of the invention to disclose the method as defined in any of the above, wherein said test fluid is a material whose rheology is controlled by regulating the proportions of a solvent or lower viscosity component and a higher viscosity component.

It is a further object of the invention to disclose the method as defined in any of the above, wherein said test fluid is a material whose rheology is controlled by evaporation of a volatile component.

It is a further object of the invention to disclose the method as defined in any of the above, wherein said test fluid is a liquid/solid mixture whose rheology is controlled by changing a ratio of liquids to solids within said mixture.

It is a further object of the invention to disclose the method as defined in any of the above, wherein said test fluid is a material whose rheology is controlled by addition of a rheology modifier or viscosifier.

It is a further object of the invention to disclose the method as defined in any of the above, wherein said test fluid is an emulsion having a droplet size distribution, said emulsion having a rheology that is controlled by modification of said droplet size distribution. In some embodiments of the method, it comprises modifying said droplet size distribution. In some preferred embodiments of the invention, said step of modifying said droplet size distribution comprises modifying said droplet size distribution by a technique selected from the group consisting of mixing said emulsion in a mixer; homogenizing said emulsion in a homogenizing device; and adding an emulsifier.

It is a further object of the invention to disclose the use of the method as defined in any of the above to measure properties of a fluid flowing through a system as defined in any of the above.

BRIEF DESCRIPTION OF THE DRAWINGS

The invention will now be described with reference to the drawings, wherein.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the term "NMR spectrometer" refers to any device that uses nuclear magnetic resonance to obtain information about a test substance.

As used herein, the term "imaging NMR spectrometer" refers to an NMR spectrometer that comprises means for providing a homogeneous magnetic field, at least one radio frequency coil, and magnetic gradient coils. An example of an imaging NMR spectrometer is an MRI instrument. As is well-known in the art, MRI has been used to obtain 2D or 3D images of the interior of such diverse objects as liquids, fruits, animals, and people. With an appropriate pulse sequence, MRI can be used to obtain velocity imaging. Examples of such pulse sequences can be found in Arola, D. F.; Barrall, G. A.; Powell, R. L.; McCarthy, K. L.; McCarthy, M. J. "Use of Nuclear Magnetic Resonance Imaging as a Viscometer for Process Monitoring," Chem. Eng. Sci. 52 (1997) 2049-2057, which is hereby incorporated in its entirety by reference.

As used herein, the term "fluid" refers to any material that can flow under a predetermined set of conditions. Non-limiting examples of fluids include liquids, non-Newtonian fluids, gases, solutions of solids or gases in liquids, suspensions of solids in liquids or gases, emulsions, and yield-stress materials.

As used herein, the term "test fluid" refers to a fluid of which at least one property of interest is to be determined.

As used herein, the term "yield-stress material" refers to a material that displays solid-like behavior at rest but which is able to flow when subjected to a shear stress larger than the yield stress. Non-limiting examples of yield-stress materials are pastes and creams.

Figure 1:
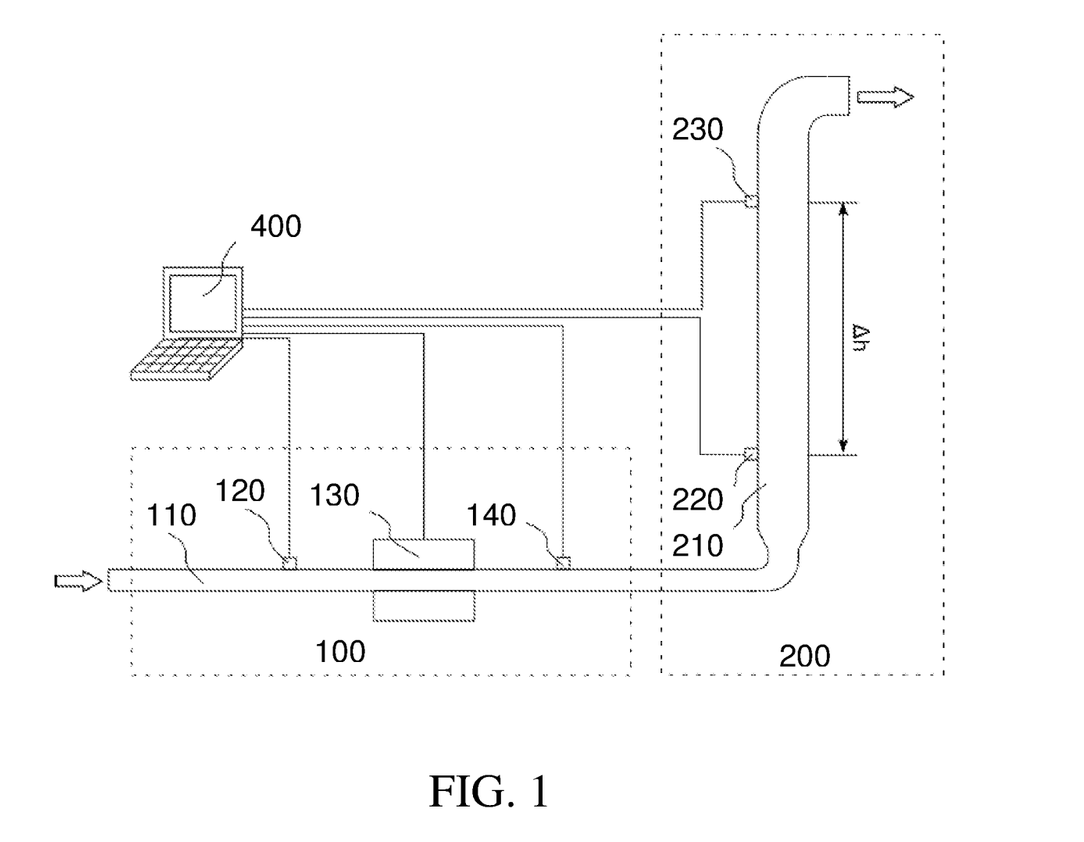
FIG. 1 presents a schematic diagram of one embodiment of the system herein disclosed; and, FIG. 2 presents a schematic diagram of a second embodiment of the system herein disclosed, which comprises an additional subsystem dedicated to measurement of the flow rate.

Reference is now made to FIG. 1, which presents a schematic diagram of one embodiment of the system disclosed herein. The system comprises a rheology subsystem 100 for measuring flow rate and rheology (or viscosity), and a density subsystem 200.

Rheology subsystem 100 comprises a horizontal tube of internal radius $r_H$ (110). The flow rate of the fluid through the horizontal tube is measured by a velocity profile measurement device 130. The velocity profile measurement device can be any appropriate device known in the art. In some embodiments, a pitot tube array or array of thermal flow sensors is used. In preferred embodiments, it is a device that measures the velocity profile non-invasively; non-limiting examples of such devices include devices that use ultrasonic, optical, or nuclear resonance devices. As described in detail below, in the most preferred embodiments, the velocity profile measurement device is an imaging NMR spectrometer (MRI).

The rheology subsystem further comprises means for determining wall shear stress. In some embodiments of the invention, the wall shear stress is determined by differential pressure measuring means. In the embodiment illustrated in FIG. 1, the differential pressure measuring means comprises two pressure sensors for measuring the pressure of the fluid in the horizontal tube, one of which (120) measures the pressure at a point upstream of the velocity profile measurement device and the other of which (140) measures the pressure downstream of the velocity profile measurement device. In other embodiments of the rheology subsystem, not illustrated in FIG. 1, the differential pressure measuring means comprises a single differential pressure sensor that measures the pressure difference between two points, one of which is upstream of the velocity profile measurement device and the other of which is downstream of the velocity profile measurement device. In yet other embodiments of the invention, also not illustrated, the means for wall shear stress comprise a sensor that measures the wall shear stress directly. Any sensor known in the art capable of making such measurements of the test fluid can be used. An example of such a sensor is disclosed in U.S. Pat. No. 7,921,731, which is hereby incorporated by reference in its entirety.

In the most preferred embodiments of the rheology subsystem, the velocity profile measurement device is an imaging NMR spectrometer (e.g. an MRI). In these embodiments, the horizontal tube (or at least that portion thereof that passes through the imaging NMR spectrometer) must be made of NMR-compatible material such as glass, ceramic, or plastic, and must not contain conductive fillers that can interfere with the transmission of RF pulses from the RF coils to the fluid inside the tube. In particularly preferred embodiments, the imaging NMR spectrometer is one that is capable of performing a pulsed gradient spin echo (PGSE) sequence that can produce a velocity image of the fluid inside the tube. In some embodiments, the imaging NMR spectrometer is a permanent-magnet device. Such NMR instruments (some of which are portable) are particularly well-suited for field measurements, for example of fluid being drawn from an oil well or pumped into an oil well.

The system further comprises density measurement subsystem 200, which is in fluid connection with the rheology subsystem. In some embodiments, the system additionally comprises a pump 610 (not included in the embodiment illustrated in FIG. 1) that is configured to pump fluid through both the horizontal tube and the vertical tube in order to ensure a constant and controllable flow rate. The pump may be located anywhere in the flow system (e.g. between the rheology and density subsystems, upstream of both the horizontal tube and the vertical tube, or downstream of both the horizontal tube and the vertical tube) that will enable it to pump fluid through both tubes. Use of a well-controlled flow rate through the rheology subsystem ensures that the rheological data generated is within the range of shear stresses and/or shear rates of interest for the specific process being monitored.

The density measurement can be made either with the fluid flowing through the vertical tube or with the flow stopped (i.e. a hydrostatic measurement). In the embodiment shown in FIG. 1, the density measurement subsystem comprises a vertical tube 210 of internal radius $r_V$. In preferred embodiments of the invention, $r_V > r_H$ for reasons explained in detail above. The density measurement subsystem further comprises a third pressure sensor 220 that measures the pressure at a location $y_1$ within the vertical tube and a fourth pressure sensor 230 that measures the pressure at a second location $y_2$ within the vertical tube, $y_2$ and $y_1$ being separated by a vertical distance $\Delta h$.

While in the embodiment shown in FIG. 1, the density measurement subsystem is located downstream of the rheology subsystem, there is no requirement that it be so. In other embodiments of the system, the density measurement subsystem is located upstream of the rheology subsystem.

In some embodiments of the system, it further comprises a pump that pumps the test fluid from the upstream subsystem to the downstream subsystem, thereby ensuring a constant flow of the test fluid.

In some embodiments of the invention, such as the embodiment illustrated schematically in FIG. 1, the system also comprises a control subsystem 400. The control subsystem comprises means for reading the pressure sensors and for controlling the velocity profile measurement device. In general, the control subsystem will comprise a computer with software and (if necessary) hardware of any appropriate type known in the art for controlling the various devices that make up the system and for reading and recording the outputs of the devices, e.g. commercially available software and hardware provided by the manufacturers of the pressure sensors and velocity profile measurement device. In preferred embodiments of the invention, the control subsystem also comprises means for storing the outputs of the various devices (pressure readings, data output of the velocity profile measurement device, etc.) that comprise the system. In preferred embodiments of the invention, the control subsystem also comprises numerical calculation means (e.g. commercially-available software or hardware) for performing the calculations and mathematical operations necessary to convert the raw data obtained from the devices that make up the system into the physical parameters (flow rate, rheology or viscosity, density) sought by the user of the system. Such mathematical operations may include, but are not limited to, integration, differentiation, unit conversions, computing fluid density, and computing rheological properties. Specific examples of algorithms for computing density and rheology are given below.

In various embodiments of the invention, outputs of the controller subsystem 400 are in the form of analog or digital electrical or optical signals. These signals can be communicated to a plant control system, presented as numbers or graphics on a display, or printed out for use by a plant operator in units chosen by the operator. In some embodiments of the invention, the controller subsystem is programmed to output parameters from the rheograms of interest for the user. These output parameters can be used in fits of common rheological models for the flow curve $\tau(\dot{\gamma})$. Non-limiting examples of such models include Newtonian, Bingham, Power-law, Herschel-Bulkley, Cross, Ellis, and Carreau.

In some embodiments of the system, additional parameters are output by the controller. Non-limiting examples of these parameters include viscosities at selected shear rates $\eta(\dot{\gamma})$ and quantities of practical interest that can be easily computed from the rheograms. One example of the alternative quantities is a set of "RPM" and "Readouts from a Fann viscometer" used in oil drilling operations. These quantities are obtained respectively by multiplication of shear rates and shear stresses by well-known constants.

In preferred embodiments of the system, the rheology subsystem is arranged such that the fluid flow through the horizontal tube is laminar. For high viscosity fluids, this condition is fairly easily met. Means for ensuring that the flow through the horizontal tube will be laminar are well-known in the art. For example, the methods described in Guzel et al., "Predicting Laminar-Turbulent Transition in Poiseuille Pipe Flow for non-Newtonian Fluids," *Chem. Eng. Sci.* 64 (2009) 254-264, which is hereby incorporated by reference in its entirety, may be used.

In preferred embodiments of the system, the pressure sensors 120, 140, 220, and 230 are sufficiently far away from fittings, bends, expansions, or contractions that they will not be affected by any disruptions from unidirectional flow caused thereby. Methods for computing the necessary distances are known in the art, for example, in Poole and Ridley, "Development-Length Requirements for Fully Developed Laminar Pipe Flow of Inelastic non-Newtonian Liquids," *J. Fluid Eng.-T ASME* 129 (2007) 1281-1287, which is hereby incorporated by reference in its entirety.

It is also within the scope of the invention to disclose a method for in-line, real-time measurements of the rheology (viscosity) and density of a test fluid. As will be apparent from the description of the method, it is most efficiently performed in the system described in detail above.

In the method herein disclosed, rheology measurements are made in a rheology subsystem, in preferred embodiments, the rheology subsystem shown schematically in FIG. 1. A test fluid flows through a horizontal tube of internal radius $r_H$. In preferred embodiments of the method, the fluid flows under conditions of laminar flow. The test fluid flows through or past a velocity profile measurement device 130. While any velocity profile measurement device known in the art that is appropriate for the test fluid can be used, in preferred embodiments of the method, the velocity profile measurement device is an NMR spectrometer. In embodiments in which an NMR spectrometer is used, that portion of the horizontal tube that flows through the NMR spectrometer is made of an NMR-compatible material.

The velocity profile measurement device is used to measure a velocity profile v(r) that represents the fluid velocity as a function of radius at a location $x_0$ along the horizontal tube. Any method known in the art for measuring such a velocity profile can be used. The volumetric flow rate Q is obtained by integration of the velocity profile; $Q=2\pi\int_0^{r_H} v(r) r\, dr$. The integration can be performed numerically (e.g. by using a computer) by any method known in the art. In preferred embodiments of the invention, the calculation is done using a controller 400 that comprises the appropriate hardware and software to control and monitor the components of the system and to perform any necessary calculations. The volumetric flow rate can be provided to the user in any convenient units; conversion from the raw units of the initial calculation (which will depend on the units used for r and v) is readily done by multiplication by an appropriate conversion factor; in preferred embodiments, conversion factors are taken from a database stored in the memory of the controller 400.

The next step in the rheology measurements is the differentiation of the velocity profile as a function of radius $r_H$ to obtain the shear rate $\dot{\gamma}(r)$, $$\text{i.e. } \dot{\gamma}(r) = \left|\frac{dv}{dr}\right|.$$

Again, the differentiation can be done numerically by any method known in the art (e.g. by using a controller or other computer).

The pressure difference $\Delta P_H$ between the pressures of the test fluid is then measured between two locations, measuring a pressure difference between pressures of said test fluid measured at two locations $x_1$ and $x_2$, where $x_1$ is upstream of $x_0$ and $x_2$ is downstream of $x_0$. The pressure difference can be measured by a pair of pressure sensors (e.g. 220 and 230) or by a single differential pressure sensor. As explained above, the pressure sensors must be sufficiently distant from fittings, bends, expansions, or contractions of the tubes such that any disruption in the unidirectional flow through the tube caused thereby will be sufficiently small so as not to interfere with the pressure measurements.

The shear stress as a function of shear rate (rheogram) $\tau(\dot{\gamma})$ is then determined First, shear stress as a function of radius $\tau(r)$ is calculated from the pressure difference and the distance L between the two pressure measurements (i.e. $L=x_2-x_1$), $$\tau(r) = \frac{\Delta P_H}{2L} r.$$

The shear stress as a function of radius is then combined with the shear rate as a function of radius to produce a rheogram (curve of shear stress as a function of shear rate). The rheological information is usually presented in the form of a rheology parameter $\eta(\dot{\gamma})$, where $$\eta(\dot{\gamma}) = \frac{\tau(\dot{\gamma})}{\dot{\gamma}}.$$

If wall stress $\tau_w$ is measured directly, without using pressure transducers, the shear stress as a function of radius is calculated as $$\tau(r) = \tau_w \frac{r}{r_H}$$

Where $r_H$ is the pipe radius,

As with the flow rate, the other parameters (shear stress, shear rate, rheogram, etc.) can be presented in any convenient units desired by the user from a database of conversion factors retained in the memory of the control unit, or, in some embodiments, by direct calculation using conversion factors input by the user.

It is noted that the rheology method herein disclosed is velocimetric, that is, the flow field inside the tube is measured directly by a spatially resolved sensor. This method has the advantage that it can produce rheograms in a single measurement, in contrast to methods such as the use of capillary rheometers, which require several measurements at different flow rates and pressure drops in order to provide the rheogram and rheology parameter.

It is further noted that the rheology method herein disclosed does not require that the horizontal tube be of circular cross section. In some embodiments of the invention, the rheology measurement is done in a channel with thin slit geometry. In this geometry, the fluid flow can be treated as flow between two infinite parallel plates. The mathematical treatment necessary to obtain the velocity profile, shear rate, shear stress, and rheology parameter differs slightly from that given above, but is well-known in the art, and is disclosed in Degre et al., "Rheology of Complex Fluids by Particle Image Velocimetry in Microchannels," *Appl. Phys. Lett.* 89 (2006) 024104, which is hereby incorporated in its entirety by reference.

The method also includes steps of determining the density p of the test fluid. The fluid flows from the horizontal tube into a vertical tube of internal radius $r_V$. The density measurements can be made hydrostatically in the vertical tube or while the fluid is flowing through it. In preferred embodiments of the invention, $r_V > r_H$, as discussed above.

In one embodiment of the method, a pressure difference $\Delta P_V$ is determined between two locations $y_1$ and $y_2$ separated by a vertical distance $\Delta h$. The pressure difference can be measured by two pressure sensors 220 and 230, as shown in FIG. 1. The density of the test fluid is then calculated (e.g. by the computer within the control subsystem) as $$\rho = \frac{1}{g\Delta h}\left(\frac{2\tau_w}{r_V}|\Delta h| - \Delta P_V\right),$$

where $\tau_W$ is the wall stress within the vertical tube and g is the acceleration due to gravity.

This expression for the density can be derived as follows. The pressure difference $\Delta P_V$ has two components, one due to hydrostatic effects and one due to frictional pressure losses, $$\text{i.e. } \Delta P_V = -\rho g \Delta h + \frac{2|\Delta h|}{r_V}\tau_W,$$

where $\tau_W$ is the wall stress in the vertical tube. The sign of the hydrostatic component depends on the relative heights of the two locations, as reflected in the sign of $\Delta h$. The sign of the purely frictional component is constant, always causing a loss in pressure as the fluid moves from an upstream location to a downstream location, thus we use the absolute value $|\Delta h|$. The density $\rho$ is calculated by rearranging the expression for $\Delta P_V$.

Calculating the density thus requires knowing the wall stress. If $r_V$ is not identical to $r_H$, which is the case in preferred embodiments of the invention, then calculating the wall stress will require information regarding the rheology of the test fluid. Note that in methods known in the prior art, in general, this rheology information will not be known, while in the method herein disclosed, it will have been determined in the prior steps of the method.

One method for determining the wall stress is to calculate it from the relation, well-known in the art, $$Q = \frac{\pi r_V^3}{\tau_W^3} \int_0^{\tau_W} |\dot{\gamma}| \tau^2 d\tau$$

(see, for example, Macosko, C. W., *Rheology Principles, Measurements and Applications*, VCH: New York, 1993, which is hereby incorporated by reference in its entirety). The equation can be solved iteratively, varying $\tau_W$ until the calculated value of Q matches the value determined during the rheology measurements. Alternatively, a table can be constructed of Q as a function of $\tau_W$, and the value of $\tau_W$ found from the value of Q determined during the rheology measurements, or by interpolation (linear or non-linear) from values of Q listed in the table. These calculations can easily be done in embodiments that include a controller subsystem or on a separate computer using commercially available software.

Figure 2:
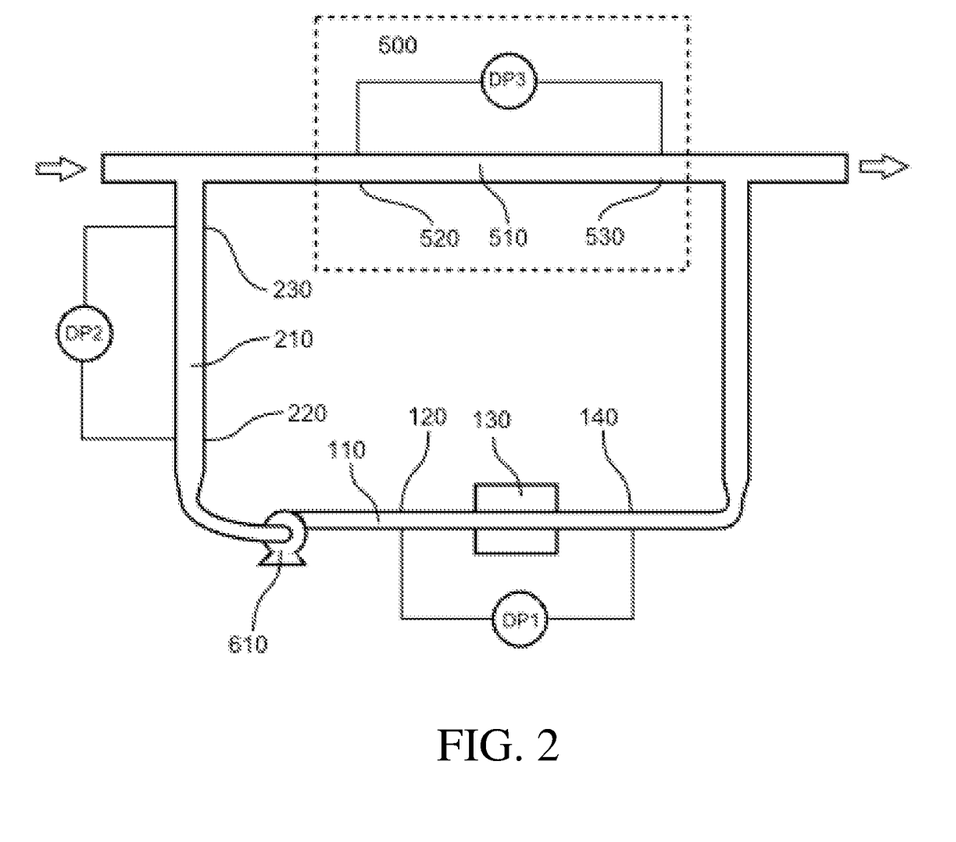

Reference is now made to FIG. 2, which presents schematically a second embodiment of the system disclosed herein. In the embodiment depicted, the density subsystem is located upstream of the rheology subsystem. In the embodiment shown in FIG. 2, pump 610 is located between the density and rheology subsystems in order to ensure a constant and controllable fluid flow rate.

The embodiment depicted in FIG. 2 comprises a dedicated subsystem 500 for measurement of the flow rate. Embodiments that include a separate subsystem for measurement of the flow rate have the advantage that they can measure much larger flow rates than are typically possible when the flow rate is measured in a rheology subsystem that passes through an imaging NMR spectrometer. The flow rate subsystem 500 comprises a tube 510 through which the test fluid flows and differential pressure measurement means 520/530 for determining the pressure drop in the fluid between two points along the flow. In the embodiment illustrated in FIG. 2, a single differential pressure sensor is used; in other embodiments, two individual pressure sensors 520 and 530 are used, and the difference in the measured pressures calculated. Fluid flows to the density and rheology subsystems via a tube that branches off from tube 510. In methods that use this embodiment of the system, rheology is determined as described above. The flow rate through tube 510 is then computed based on the rheological data obtained by using the equation $$Q = \frac{\pi r_V^3}{\tau_W^3} \int_0^{\tau_W} |\dot{\gamma}| \tau^2 d\tau,$$

where the wall shear stress $\tau_W$ is computed from the pressure drop determined by the differential pressure measurement means. The flow through the density and rheology subsystems rejoins the flow through tube 510 at a point either downstream of 530 (as shown in FIG. 2) or, in some embodiments, upstream of 520. In the case in which the outlet of subsystems 100 and 200 is located upstream of 520, the flow rate measured in subsystem 500 is the net flow rate that exits the entire system.

For best results, the wall shear stress in tube 510 must be less than or equal to the wall shear stress in tube 110. Adherence to this condition ensures that the rheological data measured in rheology subsystem 100 will cover the entire range of shear rates and shear stresses present in tube 510.

We claim:

1. A method for performing inline rheology and density measurements on a test fluid having a density $\rho$, comprising:
    flowing said test fluid through a horizontal tube of internal radius $r_H$ having an upstream end and a downstream end;
    measuring, via a velocity profile measurement device, a velocity profile v(r) at a distance $x_0$ from said upstream end for at least one value of r, $0 \leq r \leq r_H$;
    determining, via a processor, a shear rate $\dot{\gamma}(r)$;
    calculating radius-dependent shear stress as a function of shear rate (rheogram) $\tau(\dot{\gamma})$ for at least one value of r, $0 \leq r \leq r_H$;
    calculating at least one rheology parameter of said test fluid $$\eta(\dot{\gamma}) = \frac{\tau(\dot{\gamma})}{\dot{\gamma}};$$

flowing said test fluid through a vertical tube of internal radius $r_V$;
    measuring, via a first pressure sensor, a first pressure of said test fluid within said vertical tube at a location $y_1$;
    measuring, via a second pressure sensor, a second pressure of said test fluid within said vertical tube at a location $y_2$; and
    determining, via the processor, said density p of said test fluid in said vertical tube based on the first measured pressure and the second measure pressure.

2. The method according to claim 1, wherein said step of determining a shear rate comprises differentiating said velocity profile with respect to radius, $$\dot{\gamma}(r) = \left|\frac{dv}{dr}\right|.$$

3. The method according to claim 1, wherein said step of calculating a radius-dependent shear stress comprises:
    measuring a pressure difference $\Delta P_H$ between pressures of said test fluid measured at two locations $x_1$ and $x_2$, $x_1$ upstream of $x_0$, $x_2$ downstream of $x_0$;
    calculating shear stress as a function of radius $$\tau(r) = \frac{\Delta P_H}{2L} r,$$

where $L = x_2 - x_1$; and, combining said shear stress as a function of radius with said shear rate as a function of radius to produce a rheogram (curve of shear stress as a function of shear rate).

4. The method according to claim 1, wherein said step of flowing said test fluid through a horizontal tube comprises flowing said test fluid through a horizontal tube under conditions of laminar flow.

5. The method according to claim 1, wherein said step of measuring a velocity profile comprises using a velocity profile measurement device selected from the group consisting of an imaging NMR spectrometer; an ultrasound velocimetry system; an optical velocimetry system; a pitot tube array; and an array of thermal flow sensors to measure said velocity profile.

6. The method according to claim 1, wherein said test fluid is selected from the group consisting of single-component liquids, mixtures of liquids, solutions, suspensions, emulsions, colloids, slurries, pastes, creams, foams, media containing one or more liquids mixed with gas bubbles, media containing one or more liquids mixed with solid matter, and media containing one or more liquids mixed with gas and solid matter.

7. The method according to claim 1, wherein said test fluid is non-Newtonian, a yield-stress material, a potable liquid, an edible non-liquid material that can be pumped through a tube, or any combination thereof.

8. The method according to claim 1, wherein said test fluid comprises a fluid selected from the group consisting of oil-based drilling fluid, water-based drilling fluid, synthetic drilling fluid, fracturing fluid, crude oil, refined oil, an oil/water mixture, any of the above containing particulate matter, and any of the above to which a viscosifier has been added.

9. The method according to claim 1, wherein said test fluid is a potable liquid.

10. The method according to claim 1, wherein said step of measuring a velocity profile comprises:
    passing said test fluid through an imaging NMR spectrometer; and,
    imaging said test fluid as it passes through said imaging NMR spectrometer.

11. The method according to claim 10, wherein said step of imaging said test fluid comprises imaging said test fluid by using an NMR imaging technique comprising a pulsed gradient spin echo sequence.

12. The method according to claim 10, wherein said step of passing said test fluid through an imaging NMR spectrometer comprises passing said test fluid through an NMR spectrometer comprising a permanent magnet.

* * * * *